United States Patent
Mueller

(10) Patent No.: US 8,968,357 B2
(45) Date of Patent: Mar. 3, 2015

(54) COLLET BASED LOCKING MECHANISM

(75) Inventor: Peter Michael Mueller, Frederick, CO (US)

(73) Assignee: Covidien LP, Mansfield, MA (US)

(*) Notice: Subject to any disclaimer, the term of this patent is extended or adjusted under 35 U.S.C. 154(b) by 587 days.

(21) Appl. No.: 12/876,680

(22) Filed: Sep. 7, 2010

(65) Prior Publication Data

US 2012/0059408 A1 Mar. 8, 2012

(51) Int. Cl.
*A61B 17/00* (2006.01)
*A61B 17/29* (2006.01)
*A61B 18/14* (2006.01)
*A61B 18/00* (2006.01)

(52) U.S. Cl.
CPC .............. *A61B 17/29* (2013.01); *A61B 18/1445* (2013.01); *A61B 2017/00314* (2013.01); *A61B 2017/00327* (2013.01); *A61B 2017/2908* (2013.01); *A61B 2017/2927* (2013.01); *A61B 2017/2946* (2013.01); *A61B 2018/00172* (2013.01)
USPC .......................................... 606/206; 600/104

(58) Field of Classification Search
CPC .............. A61B 17/29; A61B 18/1445; A61B 2017/00314; A61B 2017/00327; A61B 2017/2908; A61B 2017/2927; A61B 2017/2946; A61B 2017/00172
USPC ......... 606/205, 206, 207, 208, 209, 210, 211, 606/51, 52, 167, 168, 169, 170; 600/104
See application file for complete search history.

(56) References Cited

U.S. PATENT DOCUMENTS

| | | |
|---|---|---|
| 5,547,117 A | 8/1996 | Hamblin et al. |
| 5,673,840 A | 10/1997 | Schulze et al. |
| 6,171,316 B1 | 1/2001 | Kovac et al. |
| 6,560,939 B2 | 5/2003 | Sorkin |
| 6,565,508 B2 | 5/2003 | Scirica et al. |
| 6,663,641 B1 | 12/2003 | Kovac et al. |
| 6,666,854 B1 | 12/2003 | Lange |
| 6,858,005 B2 | 2/2005 | Ohline et al. |
| 7,147,650 B2 | 12/2006 | Lee |
| 7,207,090 B2 | 4/2007 | Mattchen |
| 7,226,444 B1 | 6/2007 | Ellman et al. |
| 7,726,082 B2 | 6/2010 | Hayes et al. |
| 2005/0187575 A1 | 8/2005 | Hallbeck et al. |
| 2007/0099500 A1 | 5/2007 | Pilvisto et al. |
| 2007/0244473 A1 | 10/2007 | Thompson et al. |
| 2007/0250113 A1* | 10/2007 | Hegeman et al. ............. 606/207 |
| 2009/0069842 A1* | 3/2009 | Lee et al. ...................... 606/205 |

* cited by examiner

*Primary Examiner* — Katrina Stransky

(57) ABSTRACT

A surgical instrument includes a housing supporting first and second actuators, an elongated shaft extending distally from the housing, and an end effector supported by a distal portion of the elongated shaft. A tensile member extending through the elongated shaft is coupled to the first actuator and the end effector such that first actuator may be manipulated to induce motion of the end effector. A locking mechanism associated with the tensile member selectively impedes motion of the end effector. The locking mechanism includes a collet disposed about the tensile member and a collet clamp for receiving the collet. Receipt of the collet into the collet clamp induces radial compression of the collet to impede the motion of the tensile member therethrough. An actuation member extending through the elongated shaft induces insertion and withdrawal of the collet from the collet clamp.

17 Claims, 8 Drawing Sheets

COLLET BASED LOCKING MECHANISM

BACKGROUND

1. Technical Field

The present disclosure relates to a surgical apparatus for laparoscopic and endoscopic procedures. In particular, the disclosure relates to a surgical apparatus having a locking mechanism for maintaining a remotely-actuated component of the instrument at a particular position or orientation.

2. Background of Related Art

Typically in a laparoscopic, an endoscopic, or other minimally invasive surgical procedure, a small incision or puncture is made in a patient's body. A cannula is then inserted into a body cavity through the incision, which provides a passageway for inserting various surgical devices such as scissors, dissectors, retractors, or similar instruments. To facilitate operability through the cannula, instruments adapted for laparoscopic surgery typically include a relatively narrow shaft supporting an end effector at its distal end and a housing at its proximal end. Arranging the shaft of such an instrument through the cannula allows a surgeon to manipulate actuators on the housing from outside the body to induce the end effector to carry out a surgical procedure at a remote internal surgical site. This type of laparoscopic procedure has proven beneficial over traditional open surgery due to reduced trauma, improved healing and other attendant advantages.

A steerable laparoscopic or endoscopic instrument may provide a surgeon with a range of operability suitable for a particular surgical procedure. For example, the instrument may be configured such that the end effector may be aligned with a longitudinal axis of the instrument to facilitate insertion through a cannula, and thereafter, the end effector may be caused to articulate or move off-axis as necessary to appropriately position the end effector to engage tissue. Some mechanisms for articulating the distal end of an endoscopic instrument include a pair of tension-bearing drive cables, or other tensile members with distal ends anchored to the articulating portion on opposite sides of an instrument axis. The proximal ends of the drive cables are operatively coupled to an actuator on the housing that is responsive to manipulation by the surgeon to draw one of the drive cables proximally while simultaneously permitting distal motion in the other drive cable. This motion in the drive cables induces pivotal motion of the distal end of the instrument.

When the end effector of a steerable, articulating instrument has been satisfactorily positioned and oriented, a surgeon may maintain the position and orientation of the end effector by continuously exerting the necessary forces at the housing. Alternatively, some instruments are provided with a locking mechanism that permits the surgeon to temporarily lock the orientation of the end effector so that a continuous exertion of force at the housing is not required. For example, commonly owned U.S. patent application Ser. No. 12/609, 477 describes a locking collar in the housing of an instrument that is movable to selectively lock and unlock distal articulating movement of an end effector. The locking collar described is movable into, and out of contact with a sphere in the housing. The sphere is coupled to a set of tension-bearing articulation cables and is arranged to pivot to induce the distal articulating motion. A frictional force is generated in the housing when the locking collar engages the sphere to thereby maintain the articulated position of the instrument.

When tensile members are employed to induce movement at the distal end of an instrument, the tensile members themselves may be engaged to generate a frictional force that may be used to lock or impede the distal motion. Mechanisms for engaging a tension-bearing cable have been developed for other industries such as architecture or construction, and include applications such as wall retainers, concrete reinforcement and cable stay or suspension bridges. Typically these mechanisms are employed to retain an appropriately tensioned cable. One type of cable engaging mechanism is described in the background section of U.S. Pat. No. 7,726, 082. The mechanism described includes a retaining wedge that has a conical-exterior shape that fits into a mating, tapered opening in an anchor plate. The retaining wedge is divided into circumferential segments that permit the retaining wedge to be installed around a cable such that an interior surface of the retaining wedge grips the cable. A tensioning device is employed to apply a tension to the cable, and when the tensioning device is released, the cable tends to draw the retaining wedge into the anchor plate. The tapered opening of the anchor plate tends to compress the circumferential segments onto the cable, and the cable is thereby retained.

A retaining wedge or collet may be employed to engage a tensile member in the locking mechanism of a surgical instrument. In such an application, the motion at the distal end of the instrument may be selectively and temporarily impeded.

SUMMARY

The present disclosure describes a surgical instrument including a housing supporting first and second actuators that are adapted for manipulation by a user to control the instrument. An elongated shaft extends distally from the housing to define a longitudinal axis, and an end effector adapted for surgically treating tissue is supported by a distal portion of the elongated shaft. One or more tensile members extend longitudinally through the elongated shaft, and are operatively coupled to the first actuator and the end effector such that manipulation of the first actuator induces an attendant motion of the at least one tensile member, and motion of the at least one tensile member induces an attendant motion of the end effector. The instrument also includes a locking mechanism operatively associated with the tensile members to selectively impede motion of the tensile members and the attendant motion of the end effector. The locking mechanism includes a collet disposed radially about one or more of the tensile members and a collet clamp having a void defined therein for receiving the collet. Receipt of the collet into the void induces radial compression of the collet to engage the at least one tensile member, and to impede the motion thereof. Withdrawal of the collet from the void induces radial expansion of the collet such that the collet releases the tensile member. An actuation member extends at least partially through the elongated shaft and includes a proximal end operatively coupled to the second actuator. A distal end of the actuation member is coupled to either the collet or the collet clamp such that manipulation of the second actuator induces an attendant motion of one or both of the collet and the collet clamp to insert and withdraw the collet from the void.

The distal portion of the elongated shaft may include a joint therein to permit the distal portion of the elongated shaft to articulate with respect to the proximal portion of the elongated shaft. The surgical instrument may include a pair of articulation cables operatively coupled to the distal portion of the elongated shaft such that opposed longitudinal motion in the pair of articulation cables induces an attendant articulation of the distal portion of the elongated shaft. The joint in the elongated shaft may be defined by a plurality of discrete segments pivotally arranged with respect to one another, and the void may be defined in a proximal-most segment such that the proximal-most segment defines the collet clamp.

The locking mechanism may also include a biasing member to maintain the collet within the void in normally-locked configuration. Alternatively, the locking mechanism may include a biasing member to maintain a separation of the collet from the void.

The distal end of the actuating member may be coupled to the collet clamp such that the void may be drawn over the collet upon manipulation of the second actuator. The void may include a longitudinally tapered opening such that the collet may be longitudinally wedged into the void upon manipulation of the second actuator. The collet may include a longitudinal notch to facilitate radial compression of the collet.

The end effector of the instrument may include a pair of jaw members, and one or both of the jaw members may be selectively movable between an open position substantially spaced from the other of the pair of jaw members and a closed position wherein the jaw members are closer together. One or both of the jaw members may be adapted to couple to a source of electrical energy.

According to another aspect of the disclosure, an articulating surgical instrument includes a housing and an elongated shaft extending distally from the housing. The elongated shaft includes a proximal portion defining a longitudinal axis and a distal portion including a plurality of discrete segments pivotally arranged with respect to one another to permit the distal portion to articulate relative to the proximal portion. A proximal-most segment of the plurality of segments extends distally from a distal end of the proximal portion of the elongated shaft. An end effector is supported by a distal-most segment of the plurality of segments, and the end effector is adapted for surgically treating tissue. One or more tensile members extend longitudinally through the elongated shaft, and are selectively movable in a longitudinal direction to induce an attendant pivotal motion of the distal portion of the elongated shaft. The instrument also includes a locking mechanism operatively associated with the tensile members to selectively impede motion of the tensile members and the attendant pivotal motion of the distal portion of the elongated shaft. The locking mechanism includes a collet disposed radially about one of the tensile members and a void defined in the proximal-most segment. Receipt of the collet into the void induces radial compression of the collet at a longitudinal position coincident with the proximal-most segment to engage the at least one tensile member and to impede the motion of the tensile member.

The surgical instrument may include a pair of articulation cables selectively movable in opposed longitudinal directions to induce the attendant pivotal motion of the distal portion of the elongated shaft. Each of the pair of articulation cables may include a collet disposed radially thereabout, and the proximal-most segment may include a pair of voids defined therein for receiving a respective collet.

The locking mechanism may also include a selectively movable piston, and each of the collets may be coupled to the piston such that movement of the piston induces an attendant movement of the collets into the respective voids. The locking mechanism may include a biasing member operatively engaged with the piston to maintain the collets in the respective voids in a normally-locked configuration. The collet may include a tail portion exhibiting a longitudinally tapering outer profile, and the void may include a longitudinally tapered opening.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

Figure 1:
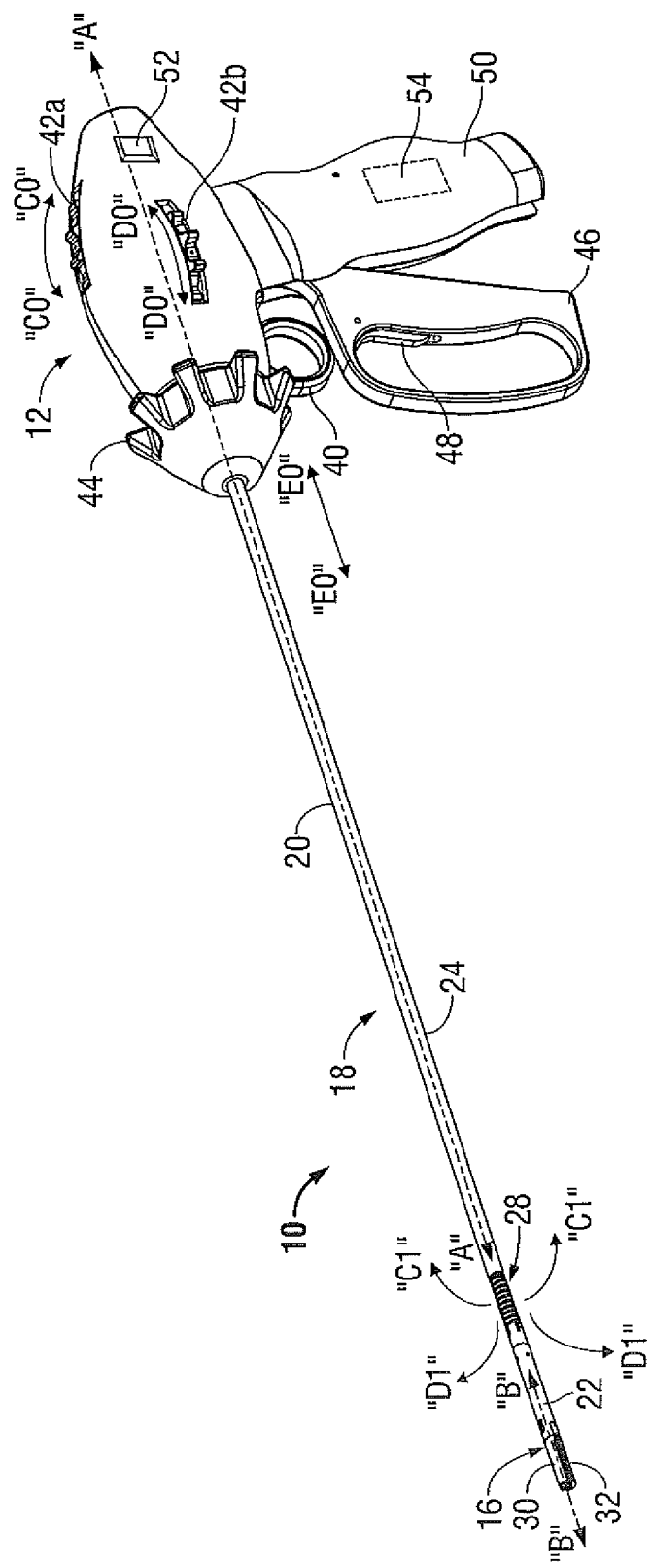
FIG. 1 is a perspective view of a surgical instrument in accordance with an embodiment of the present disclosure depicting an end effector in an aligned orientation with respect to a longitudinal axis.

Referring initially to FIG. 1, a steerable endoscopic instrument 10 is depicted generally as instrument 10. Instrument 10 includes a housing 12 near a proximal end, an end effector 16 near a distal end and an elongated shaft 18 therebetween. Elongated shaft 18 includes a proximal portion 20 extending distally from the housing 12 and an articulating distal portion 22 supporting the end effector 16. The proximal portion 20 defines a longitudinal axis A-A, and is sufficiently long to position the end effector 16 through a cannula (not shown) at an operative site. An outer tubular member 24 is provided over the proximal portion 20, and provides protection and support to the interior mechanisms therein. At least one joint 28 is established between the proximal and distal portions 20, 22 of the elongated shaft 18 permitting the distal portion 22 and the end effector 16 to articulate or pivot relative to the longitudinal axis A-A as described in greater detail below (see, e.g., FIG. 4). The end effector 16 defines an end effector axis B-B, which is aligned with the longitudinal axis A-A when the articulating distal portion 22 of the elongated shaft 18 is in a "home" configuration.

The end effector 16 includes a pair of opposing jaw members 30 and 32. The jaw members 30, 32 are operable from the housing 12 to move between a closed configuration and an open configuration (see FIG. 4). When the end effector 16 is in the closed configuration, a distal portion of each of the jaw members 30, 32 is adjacent the distal portion of the other of the jaw members 30, 32. The closed configuration allows the end effector 16 to assume a narrow profile to facilitate insertion of the end effector 16 through the cannula (not shown) into a body cavity. Inside the body cavity, the jaw members 30, 32 may be moved to the open configuration in which the distal portions of the jaw members 30, 32 are substantially spaced to receive tissue therebetween. The end effector 16 is configured for unilateral movement wherein only movable jaw member 32 moves relative to the end effector axis B-B (while stationary jaw member 30 remains stationary relative to the end effector axis B-B) as the end effector 16 is moved between the open and closed configurations. However, bilateral motion is also contemplated wherein both of the jaw members 30, 32 are configured to be moveable relative to the axis B-B.

Housing 12 is accessible by the surgeon from outside the body cavity to control the positioning, orientation and operation of the end effector 16 when the end effector 16 is positioned inside the body cavity at a surgical site. To provide this operability, the housing 12 supports various actuators that are operable to induce or prohibit movement in the end effector 16 through various modes. These actuators include a locking trigger 40, and a pair of articulation dials 42a, 42b. The articulation dials 42a, 42b are operable to pivot the distal portion 22 of the elongated shaft 18 to various articulated orientations with respect to the longitudinal axis A-A. For example, articulation dial 42a may be rotated in the direction of arrows "C0" to induce pivotal movement in a first plane, e.g., a vertical plane, as indicated by arrows "C1." Similarly, articulation dial 42b may be rotated in the direction of arrows "D0" to induce pivotal movement in a second plane, e.g., a horizontal plane, as indicated by arrows "D1." The trigger 40 is movable in a longitudinal direction as indicated by arrows "E0" between locked and unlocked positions. When the trigger 40 is in the unlocked position, e.g., a proximal position, the articulation dials 42a, 42b are functional as described above. However, when the trigger 40 is in the locked position, e.g., a distal position, the articulation dials 42a, 42b are inoperable to pivot the distal portion 22 of the elongated shaft 18 as described in greater detail below. Thus, the trigger 40 is operable to lock and maintain the end effector 16 in a particular orientation with respect to the longitudinal axis A-A.

Other actuators include shoulder roll knob 44, a pivoting handle 46 and a finger trigger 48. The shoulder roll knob 44 is operable to rotate the elongated shaft 18 about the longitudinal axis A-A, and may thus cooperate with the articulation dials 42a, 42b to permit the end effector 16 to be appropriately positioned and oriented in a three dimensional environment to effectively engage tissue. The pivoting handle 46 may be approximated and separated relative to a stationary handle 50 to move the jaw members 30, 32 between the open and closed configurations. Finger trigger 48 is operable to lock the pivoting handle 46 in an approximated position with respect to the stationary handle 50, and thus maintain the jaw members 30, 32 in the closed configuration.

When the jaw members 30, 32 are in the closed configuration, the surgeon may initiate the delivery of electrosurgical energy to the jaw members 30, 32 by manipulating a push button 52 provided on the housing 12. In alternate embodiments, the delivery of electrosurgical energy may be initiated with a footswitch (not shown) or other external actuators. Push button 52 is in electrical communication with a source of electrosurgical energy such as electrosurgical generator 54. The electrosurgical generator 54 serves to produce electrosurgical energy and also to control and monitor the delivery of the electrosurgical energy. Various types of electrosurgical generators 54, such as those generators provided by Covidien—Energy-based Devices, of Boulder, Colo., may be suitable for this purpose. Electrosurgical generator 54 may be housed within the stationary handle 50 as depicted schematically in FIG. 1, or may alternatively be electrically and mechanically coupled to the instrument 10 by a cable (not shown). The electrosurgical generator 54 is in electrical communication with at least one of the jaw members 30, 32.

Figure 2A:
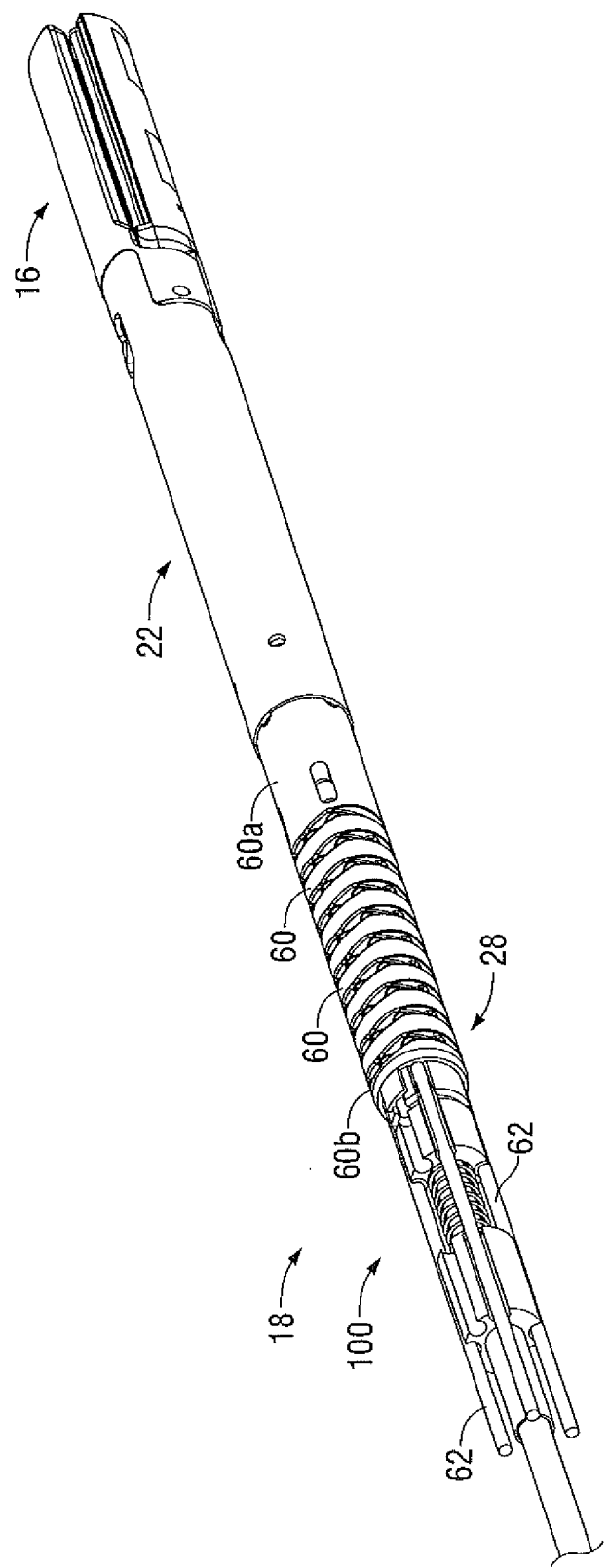
FIG. 2A is a partial, perspective view of a distal end of the instrument of FIG. 1 depicting a locking mechanism configured for maintaining the end effector in the aligned orientation.

Referring now to FIG. 2A the elongated shaft 18 is depicted with the outer tubular member 24 (FIG. 1) removed for clarity. The distal portion 22 of the elongated shaft 18 includes a plurality of discrete segments 60. Each segment 60 is pivotally arranged with respect to a neighboring segment 60 to permit the distal portion 22 to pivot relative to the longitudinal axis A-A (FIG. 1). Each segment 60 permits passage of four tensile members, such as articulation cables 62. A distal end of each of the articulation cables 62 is secured to a distal-most segment 60a, and a proximal end (not shown) of each articulation cable 62 is operatively associated with one of the articulation dials 42a, 42b (FIG. 1). The articulation dials 42a, 42b each impart opposed longitudinal motion (see FIG. 4) to a pair the articulation cables 62, and thus pivotal motion of the distal portion 22 about the plurality of segments 60. The articulation cables 62 are arranged near an outer circumference of the segments 60 and have a radial spacing of about 90 degrees. Thus, the articulation cables 62 define two orthogonal planes of articulation in which the distal portion 22 may pivot.

A locking mechanism 100 is provided to selectively engage the articulation cables 62, thereby impeding movement of the articulation cables 62 and any attendant motion of the end effector 16. Once a satisfactory articulated position or orientation of the end effector 16 has been achieved, a surgeon may employ the locking mechanism 100 to temporarily maintain the position or orientation of the end effector 16 without continuously exerting force on the articulation dials 42a, 42b (FIG. 1).

The articulation cables 62 may be constructed of stainless steel wire or other material suitable for transmitting tensile forces to the distal-most segment 60a. Regardless of the construction materials, the articulation cables 62 exhibit a spring rate that is amplified over the length of the articulation cables 62, and thus, the articulation cables 62 may tend to stretch when external loads are applied to the elongated shaft 18. This tendency to stretch may be associated with an unintended change in orientation of the distal portion 22 of the elongated shaft 18, e.g., without a corresponding movement of the articulation dials 42a, 42b initiated by the surgeon. To diminish this unintended movement of the articulation cables 62 and end effector 16, the locking mechanism 100 is provided near the distal portion 22 of the elongated shaft 18. By arresting the movement of the articulation cables 62 near the distal portion 22, the effects of the spring rate of the articulation cables 62 are relatively low. As described in greater detail below, the locking mechanism 100 is configured to selectively engage the articulation cables 62 at a longitudinal location coincident with a proximal-most segment 60b.

Figure 2B:
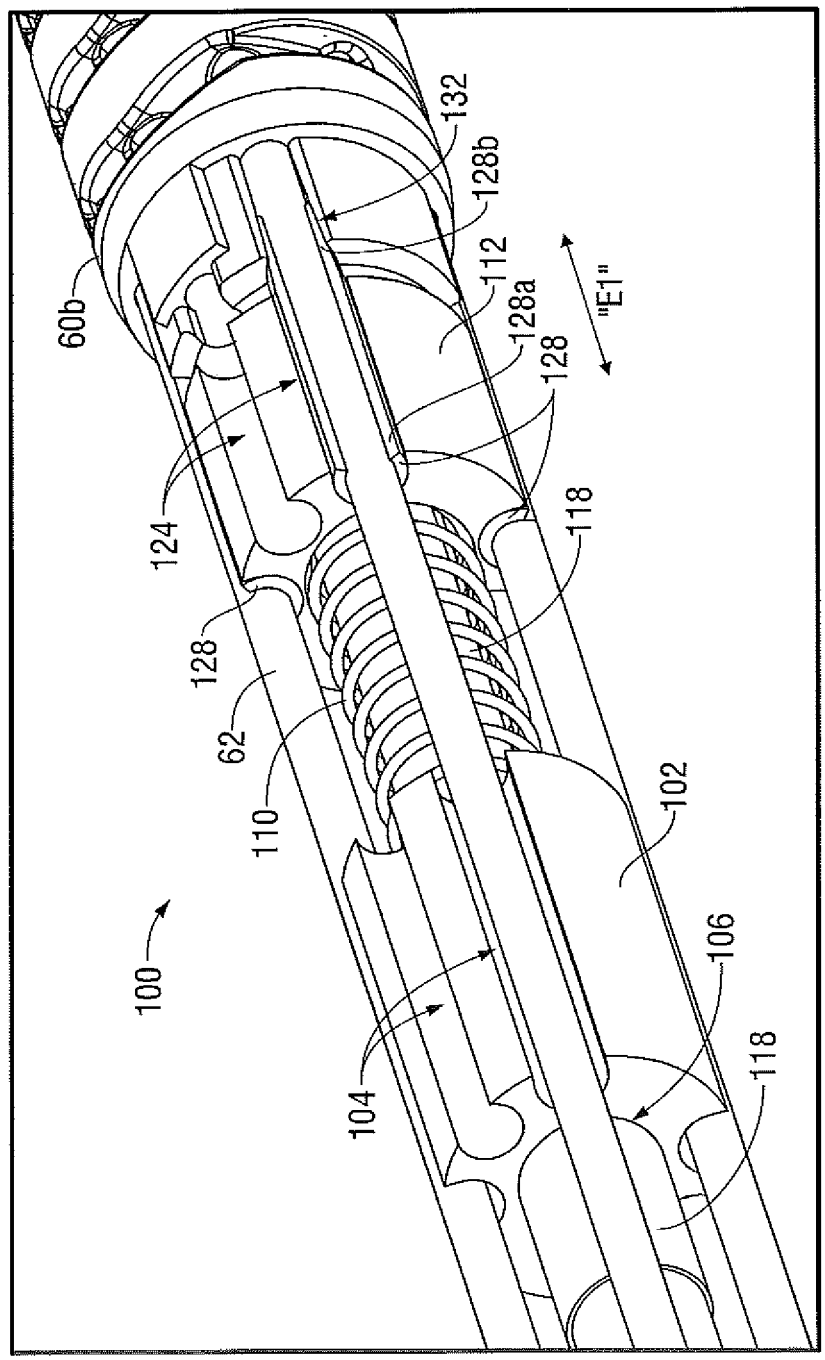
FIG. 2B is an enlarged, perspective view of the locking mechanism depicted in FIG. 2A in a locked configuration in which longitudinal motion of a set of articulation cables is prohibited.

Referring now to FIG. 2B, the locking mechanism 100 is depicted in a normally locked configuration in which longitudinal movement of the articulation cables 62 is prohibited. The locking mechanism 100 includes a base member 102 defining a fixed longitudinal reference. The base member 102 is rigidly coupled to outer tubular member 24 (FIG. 1). Thus, the base member 102 may rotate about the longitudinal axis A-A when the rotation knob 44 is rotated, but does not move longitudinally with respect to the longitudinal axis A-A. The base member 102 includes six passageways 104. Four of the passageways 104 are occupied by the articulation cables 62, which may move unencumbered therethrough when the locking mechanism 100 is in an unlocked configuration (see FIG. 3). The remaining two passageways 104 are provided for passage of other tensile members (not shown for clarity) that may be used for mechanically coupling the end effector 16 with the housing 12, e.g., to move the jaw members 30, 32 between the open and closed configurations. Alternatively or additionally, electrically conductive leads (not shown) may extend through the passageways 104 such that electrosurgical energy may be transmitted therethrough. A central bore 106 extends longitudinally through the base member 102.

A compression spring 110 abuts a distal face of the base member 102. The compression spring 110 biases a piston 112 to a distal longitudinal position. The piston 112 is configured for longitudinal movement with respect to the base member 102, and is rigidly coupled to a distal end of an actuating sleeve 118. The actuating sleeve 118 extends proximally through compression spring 110 and the central bore 106 of the base member 102, and may be induced to move unencumbered therethrough. A proximal end (not shown) of the actuating sleeve 118 is operatively coupled to the locking trigger 40 such that the surgeon may selectively impart longitudinal motion to the actuating sleeve 118 and the piston 112 in the direction of arrows "E1."

The piston 112 includes six passageways 124 corresponding to the six passageways 104 defined through the base member 102. The four passageways 124 through which the articulation cables 62 extend are equipped with collet members 128 disposed radially about respective articulation cables. Each of the collet members 128 includes a body portion 128a fixedly coupled to the piston 112, and a tapered tail portion 128b extending distally from the piston 112. The tail portions 128b exhibit an external taper, and are flexible such that the collet member 128 may be compressed radially inwardly onto a respective articulation cable 62. Longitudinal notches 128c (visible in FIG. 7) may be cut into the tail portions 128b to promote flexibility of the tail portions 128b.

The locked configuration of the locking mechanism is characterized by the tail portions 128b of the collet members 128 extending into the proximal-most segment 60b. Voids or tapered bores 132 are defined in the proximal-most segment 60b to receive respective tail portions 128b therein. The biasing force of the compression spring 110 presses the tail portions 128b longitudinally into the tapered bores 132, and the tapered bores 132, in turn, elastically deform or compress the collet members 128 radially onto the articulation cables 62. The resulting frictional force between the collet member 128 and the articulation cable 62 prohibits longitudinal movement of the articulation cable 62 and unintended articulation of the distal portion 22 of the elongated shaft. In this manner, the proximal-most segment 60b serves as a collet clamp since receipt of the collets members 128 into the tapered bores 132 clamps the collets 128 onto the respective articulation cables 62.

Figure 3:
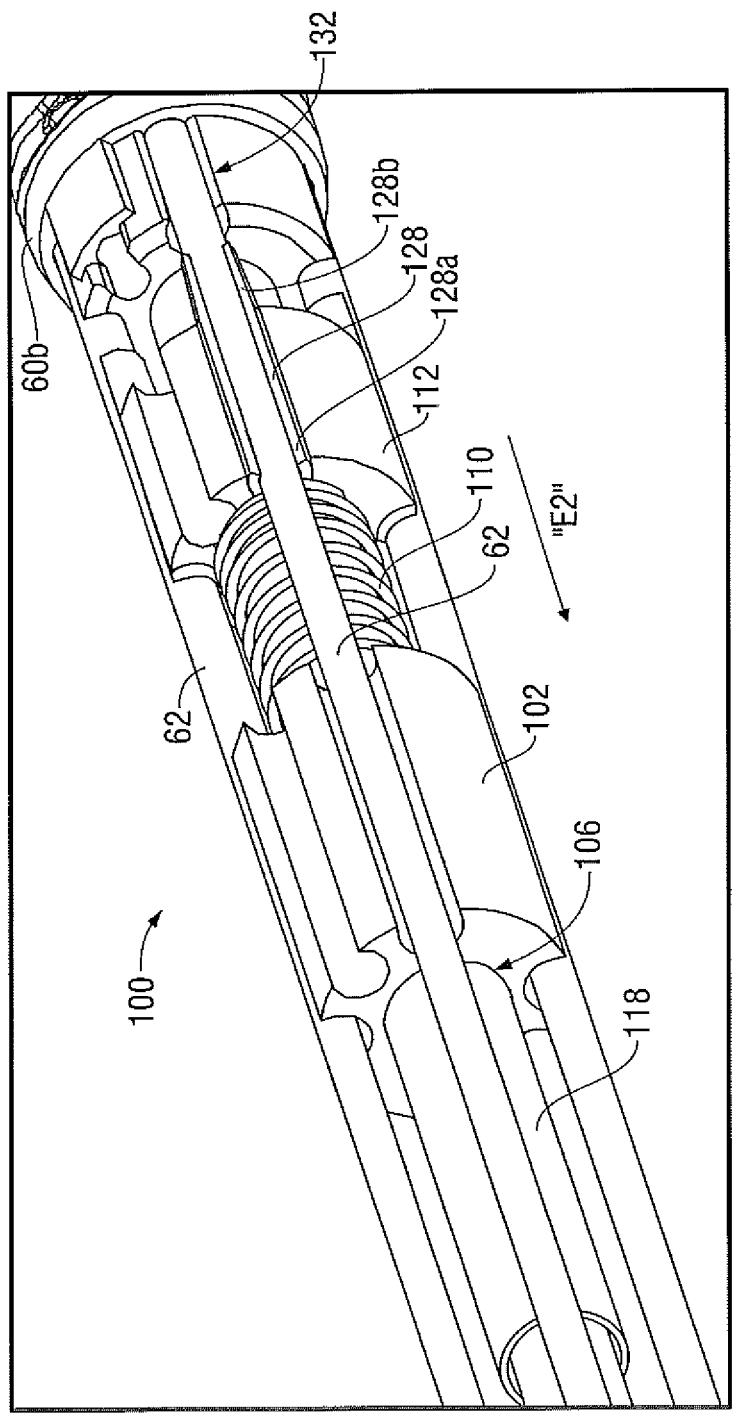
FIG. 3 is a perspective view of the locking mechanism in an unlocked configuration in which longitudinal motion of the articulation cables is permitted.

As depicted in FIG. 3, the locking mechanism 100 may be moved to an unlocked configuration to permit longitudinal motion of the articulation cables 62 and corresponding pivotal motion of the distal portion 22 of the elongated shaft 18. The surgeon may draw the actuating sleeve 118 proximally through central bore 106 in the direction of arrow "E2" by actuating the locking trigger 40 (FIG. 1). The piston 112 is thus drawn proximally against the bias of compression spring 110, and the tail portions 128b of the collet members 128 are drawn out of the tapered bores 132 of the proximal-most link 60b. Unconstrained by the proximal-most link 60b, the tail portions 128b are permitted expand elastically in a radial direction away from the articulation cable 62. Thus, the frictional forces between the collet members 128 and the articulation cables 62 are reduced such that the articulation cables 62 may be induced to slide longitudinally through the collet members 128.

Figure 4:
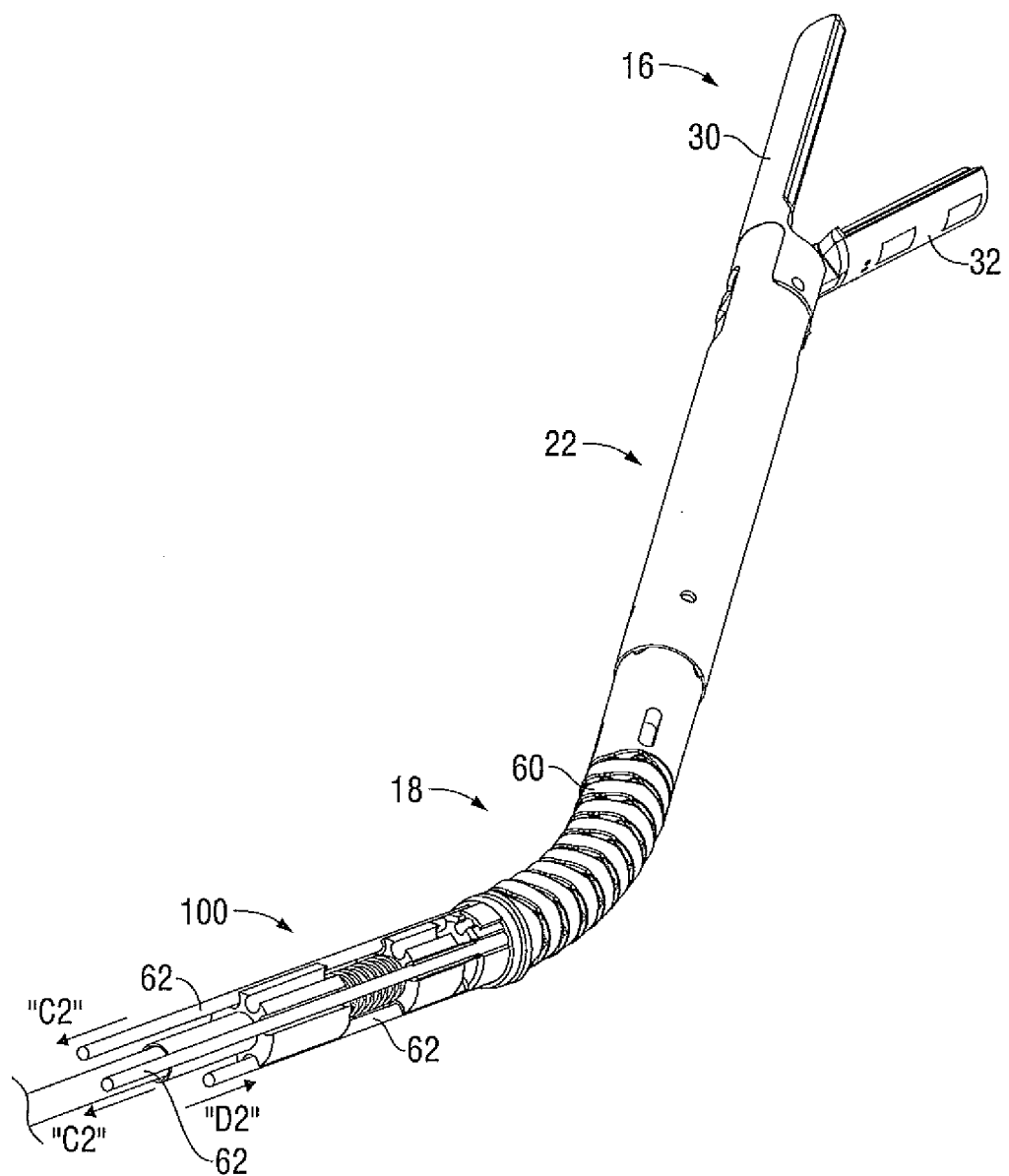
FIG. 4 is a partial, perspective view of the distal end of the instrument of FIG. 1 in which the articulation cables are moved to move the end effector to an articulated orientation with respect to the longitudinal axis.

When the locking mechanism 100 is in the unlocked configuration, the distal portion 22 of the elongated shaft 18 may be articulated as depicted in FIG. 4. The surgeon may manipulate the articulation dials 42a, 42b (FIG. 1) to draw particular articulation cables 62 proximally while opposed articulation cables 62 are advanced distally as indicated by arrows "C2" and "D2." This opposed longitudinal motion in the articulation cables 62 induces pivoting of the segments 60 relative to one another, and allows the end effector 16 to be appropriately positioned and oriented relative to targeted tissue (not shown).

Figure 5:
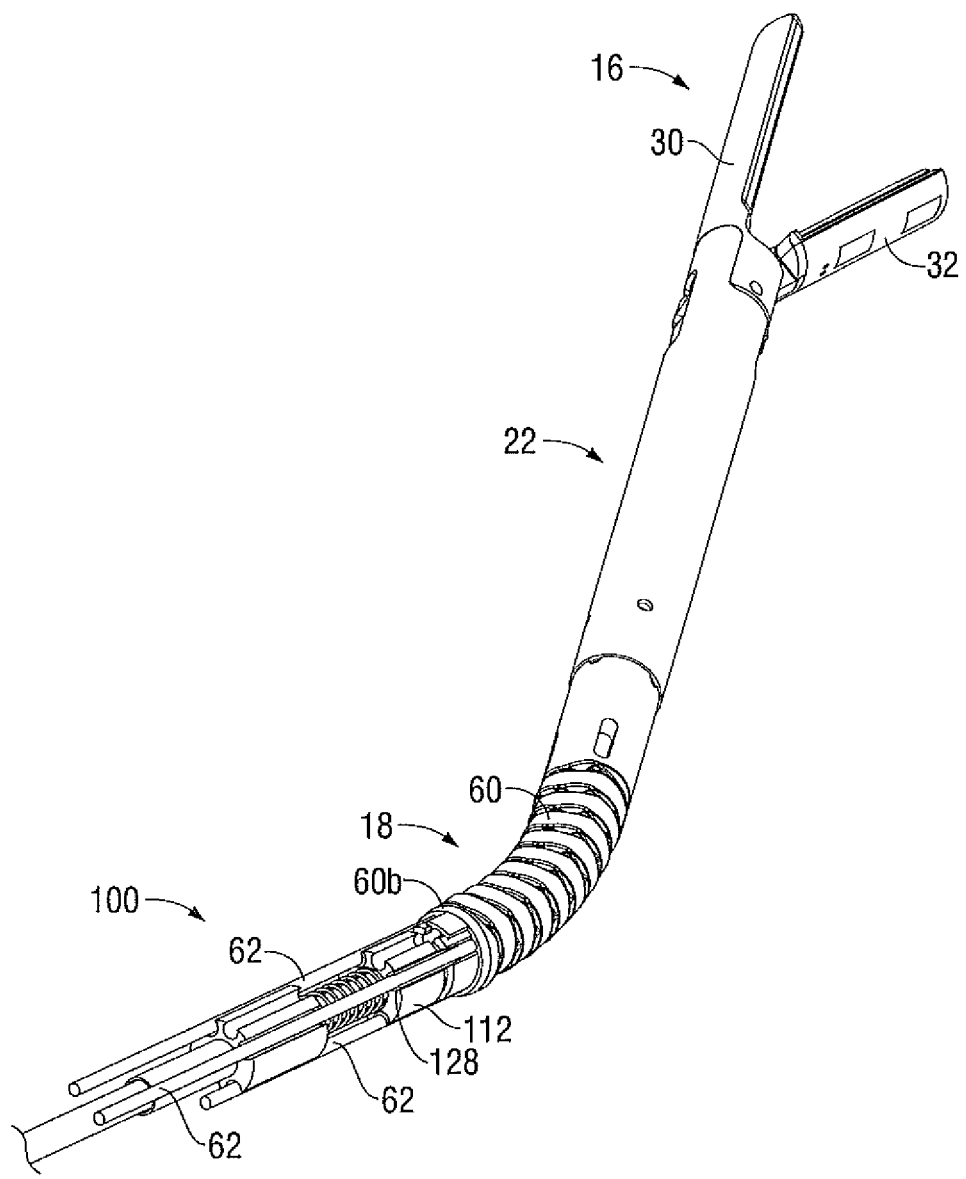
FIG. 5 is a partial, perspective view of the distal end of the instrument of FIG. 1 in which the locking mechanism is in a locked configuration maintaining the end effector in the articulated orientation.

As depicted in FIG. 5, the locking mechanism 100 may be returned to the normally locked configuration when the distal portion 22 of the elongated shaft 18 is in an articulated configuration. The surgeon may release the locking trigger 40 (FIG. 1) to permit the piston 112 to return to the distal longitudinal position under the bias of compression spring 110. When the piston 112 is in the distal longitudinal position, the collets 128 engage the proximal-most segment 60b, and the proximal-most segment 60b compresses the collet members 128 onto the articulation cables 62. Longitudinal motion of the articulation cables 62 is thus prohibited. The articulated position of the distal portion 22 of the elongated shaft 18 may be maintained, and a stable platform for the actuation of the end effector 16 is provided. For example, the jaw members 30, 32 may be closed onto tissue, and electrosurgical energy may be provided to treat the tissue without unintended motion of the end effector 16.

Figure 6:
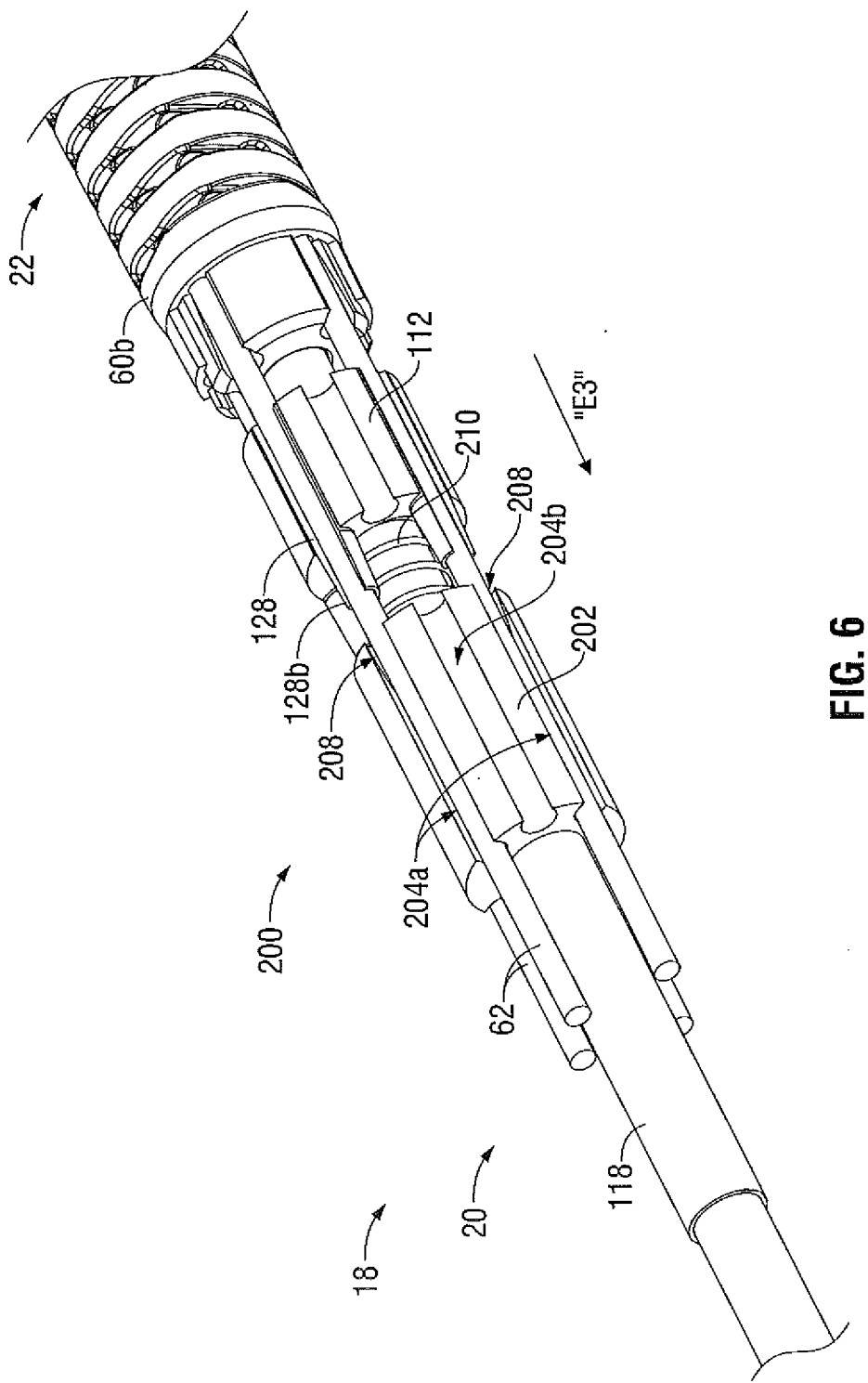
FIG. 6 is a perspective view of a locking mechanism in accordance with an alternate embodiment of the present disclosure.

Referring now to FIG. 6, an alternate embodiment of a locking mechanism 200 is depicted in a normally-unlocked configuration. The locking mechanism 200 includes base member 202 that may be rigidly coupled to outer tubular member 24 to provide a stationary longitudinal reference. The base member 202 includes six radially-spaced, longitudinal passageways 204a, 204b extending therethrough. Four of the passageways 204a are occupied by articulation cables 62 and include a tapered distal opening 208. The remaining two passageways 204b remain available for the passage of additional tensile members or electrical leads (not shown). A compression spring 210 abuts a distal face of the base member 202 and biases piston 112 to a distal longitudinal position. The piston 112 is oriented such that the flexible tail portions 128b of the collet members 128 protrude from the piston 112 in a proximal direction.

A distal end of actuating sleeve 118 is rigidly coupled to the piston 112 and a proximal end (not shown) is operatively coupled to locking trigger 40 (FIG. 1) such that the surgeon may draw the actuating sleeve 118 proximally in the direction of arrow "E3" against the bias of the compression spring 210. In this manner, the surgeon may selectively draw the collet members 128 proximally to engage the tapered openings 128 defined in the base member 202. The tail portions 128b of the collet members 128 are thus compressed radially inwardly onto a respective articulation cable 62, and the longitudinal positions of the articulation cables 62 are maintained. In this manner, the base member 202 serves as a collet clamp. The surgeon may also selectively advance the actuating sleeve 118 distally under the bias of compression spring 210 to withdraw the collet members 128 from the tapered openings 128. Withdrawal of the collet members 128 from the tapered openings 208 induces a radial expansion of the collet members 128 such that the collet members 128 release the respective articulation cables 62.

The locking mechanism 200 may be disposed at any longitudinal position within the proximal portion 20 of the elongated shaft 18. Unintended movement of the distal portion 22 of the elongated shaft 18 due to stretching of the articulation cables 62 may be mitigated by incorporating the locking mechanism 200 as close as practicable to the proximal-most segment 60b.

Figure 7:
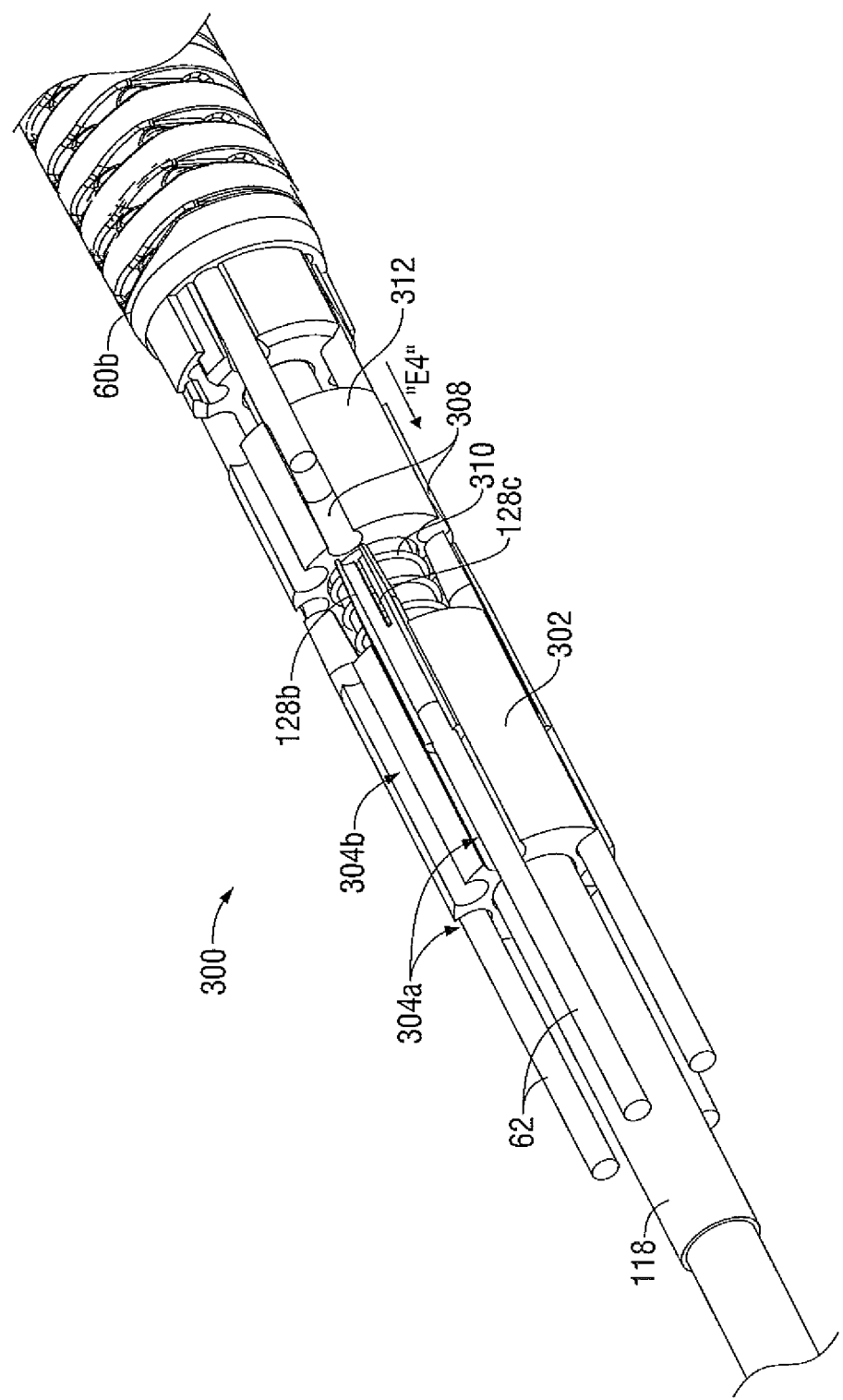
FIG. 7 is a perspective view of a locking mechanism in accordance with an additional alternate embodiment of the present disclosure.

Referring now to FIG. 7, another alternate embodiment of a locking mechanism 300 is depicted in a normally-unlocked configuration. The locking mechanism 300 includes base member 302 that may be rigidly coupled to outer tubular member 24 (FIG. 1) to provide a stationary longitudinal reference. The base member 302 includes six radially-spaced, longitudinal passageways 304a, 304b extending therethrough. Four of the passageways 304a are occupied by collet members 128 and articulation cables 62 (depicted in broken form) extending therethrough. The collet members 128 are rigidly coupled to the base member 302, and thus remain longitudinally stationary along with the base member 302. The collet members 128 are arranged such that the tail portions 128b protrude distally from the base member 302, and the tail portions 128b are permitted expand elastically in a radial direction away from the articulation cable 62. Thus, in the normally-unlocked configuration of the locking mechanism 300, the articulation cables 62 are permitted to move freely in a longitudinal direction through the collet members 128. The two passageways 304b that are not occupied by collet members 128 are available for the passage of additional tensile members or electrical leads (not shown).

A compression spring 310 abuts a distal face of the base member 302 and biases piston 312 to a distal longitudinal position. The piston 312 includes tapered openings 308 corresponding with the collet members 128. Actuating sleeve 118 is coupled to the piston 312 such that the surgeon may draw the actuating sleeve 118 and piston 312 proximally in the direction of arrow "E4" against the bias of the compression spring 310. In this manner, the surgeon may selectively move the locking mechanism 300 to a locked configuration by drawing the tapered openings 308 of the piston 312 proximally to engage the tail portions 128b of the collet members 128. The piston 312 thus serves as a collet clamp by compressing the tail portions 128b of the collet members 128 radially inwardly onto a respective articulation cable 62. Thus, in the locked configuration of the locking mechanism 300, longitudinal movement of the articulation cables 62 is prohibited.

Longitudinal notches 128c are defined in the tail portions 128b and facilitate the radial compression of the collet members 128. The external taper on the collet members 128 guide the collet members 128 into the respective voids 132, 208 and 308 included in the various embodiments described above. The voids 132, 208 and 308 are internally tapered to receive the collet members 128. Other embodiments (not shown) are envisioned in which only one of the collet members 128 and the respective void 132, 208, 308 includes a taper to allow the collet member 128 to radially deform upon longitudinal receipt in the voids 132, 208 and 308.

Although the foregoing disclosure has been described in some detail by way of illustration and example, for purposes of clarity or understanding, it will be obvious that certain changes and modifications may be practiced within the scope of the appended claims.

What is claimed is:

1. A surgical instrument, comprising:
    a housing supporting first and second actuators thereon, the first and second actuators adapted for manipulation by a user to control the instrument;
    an elongated shaft including a proximal portion and a distal portion, the proximal portion extending distally from the housing to define a longitudinal axis, the distal portion defining at least one articulation joint therein to permit the distal portion to articulate with respect to the proximal portion;
    an end effector supported at a distal end of the distal portion of the elongated shaft, the end effector adapted for surgically treating tissue;
    at least one tensile member extending longitudinally through the elongated shaft, the at least one tensile member operatively coupling the first actuator and the distal portion of the elongated shaft such that manipulation of the first actuator induces an attendant motion of the distal portion of the elongated shaft and the end effector relative to the proximal portion of the elongated shaft; and
    a locking mechanism positioned proximally of and directly adjacent the at least one articulation joint, the locking mechanism operatively associated with the at least one tensile member to selectively impede motion of the at least one tensile member to thereby impede the attendant motion of the distal portion of the elongated shaft and the end effector, the locking mechanism comprising:
        a collet disposed radially about the at least one tensile member;
        a collet clamp including a void defined therein, wherein receipt of the collet into the void induces radial compression of the collet to engage the at least one tensile member and to impede the motion of the tensile member through the collet thereby impeding attendant motion of the distal portion of the elongated shaft and the end effector relative to the proximal portion of the elongated shaft, and wherein withdrawal of the collet from the void induces radial expansion of the collet such that the collet releases the at least one tensile member thereby permitting motion of the tensile member through the collet to induce attendant motion of the distal portion of the elongated shaft and the end effector relative to the proximal portion of the elongated shaft; and
        an actuation member extending at least partially through the elongated shaft, the actuation member including a proximal end operatively coupled to the second actuator and a distal end coupled to at least one of the collet and the collet clamp such that manipulation of the second actuator induces an attendant motion of at least one of the collet and the collet clamp to insert and withdraw the collet from the void.

2. The surgical instrument according to claim 1, wherein the at least one tensile member includes at least one pair of articulation cables operatively coupled to the distal portion of the elongated shaft such that opposed longitudinal motion in the pair of articulation cables induces an attendant articulation of the distal portion of the elongated shaft and the end effector relative to the proximal portion of the elongated shaft.

3. The surgical instrument according to claim 2, wherein the at least one articulation joint is defined by a plurality of discrete segments pivotally arranged with respect to one another, and wherein the void is defined in a proximal-most segment such that the proximal-most segment defines the collet clamp.

4. The surgical instrument according to claim 3, wherein the locking mechanism further includes a biasing member to maintain the collet within the void in normally-locked configuration.

5. The surgical instrument according to claim 3, wherein the locking mechanism further includes a biasing member to maintain a separation of the collet from the void.

6. The surgical instrument according to claim 1, wherein the distal end of the actuating member is coupled to the collet clamp such that the void may be drawn over the collet upon manipulation of the second actuator.

7. The surgical instrument according to claim 1, wherein the void includes a longitudinally tapered opening such that the collet may be longitudinally wedged into the void upon manipulation of the second actuator.

8. The surgical instrument according to claim 1, wherein the collet includes a longitudinal notch to facilitate radial compression of the collet.

9. The surgical instrument according to claim 1, wherein the end effector includes a pair of jaw members, and wherein at least one of the jaw members is selectively movable between an open position substantially spaced from the other of the pair of jaw members and a closed position wherein the jaw members are closer together.

10. The surgical instrument according to claim 9, wherein at least one of the pair of jaw members is adapted to couple to a source of electrical energy.

11. An articulating surgical instrument, comprising:
a housing;
an elongated shaft including a proximal portion extending distally from the housing and defining a longitudinal axis, and a distal portion including a plurality of discrete segments pivotally arranged with respect to one another to permit the distal portion to articulate relative to the proximal portion, wherein a proximal-most segment of the plurality of segments extends distally from a distal end of the proximal portion;
an end effector supported by a distal-most segment of the plurality of segments, the end effector adapted for surgically treating tissue and configured to articulate relative to the proximal portion of the elongated shaft in conjunction with articulation of the distal portion of the elongated shaft relative to the proximal portion;
at least one tensile member extending longitudinally through the elongated shaft, the at least tensile member selectively movable in a longitudinal direction to induce an attendant pivotal motion of the distal portion of the elongated shaft and the end effector relative to the proximal portion of the elongated shaft; and
a locking mechanism positioned proximally of and directly adjacent the proximal-most segment of the plurality of segments, the locking mechanism operatively associated with the at least one tensile member to selectively impede motion of the at least one tensile member to thereby impede the attendant pivotal motion of the distal portion of the elongated shaft and the end effector relative to the proximal portion of the elongated shaft, the locking mechanism comprising:
a collet disposed radially about the at least one tensile member; and
a void defined in the proximal-most segment, wherein receipt of the collet into the void induces radial compression of the collet at a longitudinal position coincident with the proximal-most segment to engage the at least one tensile member and to impede the motion thereof thereby impeding attendant pivotal motion of the distal portion of the elongated shaft and the end effector relative to the proximal portion of the elongated shaft.

12. The surgical instrument according to claim 11, wherein the at least one tensile member includes at least one pair of articulation cables selectively movable in opposed longitudinal directions to induce the attendant pivotal motion of the distal portion of the elongated shaft and the end effector relative to the proximal portion of the elongated shaft.

13. The surgical instrument according to claim 12, wherein each of the pair of articulation cables includes a collet disposed radially thereabout, and wherein the proximal-most segment includes at least one pair of voids defined therein for receiving a respective collet.

14. The surgical instrument according to claim 13, wherein the locking mechanism further includes a selectively movable piston, wherein each of the collets is coupled to the piston such that movement of the piston induces an attendant movement of the collets into the respective voids.

15. The surgical instrument according to claim 14, wherein the locking mechanism includes a biasing member operatively engaged with the piston to maintain the collets in the respective voids in a normally-locked configuration.

16. The surgical instrument according to claim 11, wherein the collet includes a tail portion exhibiting a longitudinally tapering profile.

17. The surgical instrument according to claim 16, wherein the void includes a longitudinally tapered opening.

* * * * *